US00PP10676P

United States Patent [19]

Beat

[11] Patent Number: Plant 10,676

[45] Date of Patent: Nov. 10, 1998

[54] SWEET GUM 'CLYDESFORM'

[75] Inventor: Clyde R. Beat, Eugene, Oreg.

[73] Assignee: J. Frank Schmidt & Son Co., Boring, Oreg.

[21] Appl. No.: 781,642

[22] Filed: Jan. 10, 1997

[51] Int. Cl.[6] ..... A01H 5/00

[52] U.S. Cl. ..... Plt./51.1

[58] Field of Search ..... Plt./51.1

[56] References Cited

U.S. PATENT DOCUMENTS

P.P. 4,601 10/1980 Siebenthaler ..... Plt./51.1

P.P. 9,788 1/1997 Grant et al. ..... Plt./51.1

*Primary Examiner*—James R. Feyrer
*Assistant Examiner*—Kent L. Bell
*Attorney, Agent, or Firm*—Klarquist Sparkman Campbell Leigh & Whinston

[57] ABSTRACT

A sweet gum tree named 'Clydesform' having a columnar growth habit with a narrow overall shape and stiffly ascending branches, a relatively slow growth rate, unusually dark green summer leaf color and corky ridges which develop on vigorously growing branches during their first growing season.

1 Drawing Sheet

DESCRIPTION

The present invention relates to a new and distinct variety of sweet gum tree which is named 'Clydesform'.

I discovered my new tree as a chance seedling growing in a cultivated area of my nursery in Lane County, Oreg. Although the parentage of my new variety is unknown, it is believed to be a chance seedling from a *Liquidambar styraciflua* tree. As I observed the initially discovered tree of my new variety, my attention was drawn to this tree because of its narrow overall shape and unusually dark summer leaf color.

I observed this tree for a period of time and became quite convinced it would be a valuable new tree for landscape use becaue of its narrow columnar growth habit and stiffly ascending branches. This shape, combined with a somewhat slower growth rate, makes my new tree an ideal tree for restricted space. In addition, the unusually dark summer leaf color and corky ridges appearing early in the development of branches of my new tree contribute to the striking unique qualities of this tree.

Asexual propagation of my new tree has been performed at my direction at J. Frank Schmidt & Son Co., Boring, Oreg., by grafting onto *Liquidambar styraciflua* seedlings.

This propagation, and successive asexual propagation by grafting, and observation of the resulting progeny, have proven the characteristics of my new variety of sweet gum tree to be firmly fixed. Furthermore, these observations have confirmed that my new variety represents a new and improved variety of sweet gum tree as particularly evidenced by the unique combination of a columnar growth habit with narrow overall shape and stiffly ascending branches, a somewhat slower growth rate, unusually dark summer leaf color, and relatively early development of corky ridges on the bark of vigorously growing branches.

The accompanying photographs depict the color of the tree and foliage of my new variety, as well as the shape of the tree, as nearly true as is reasonably possible to make the same in a color illustration of this character.

Figure 1:
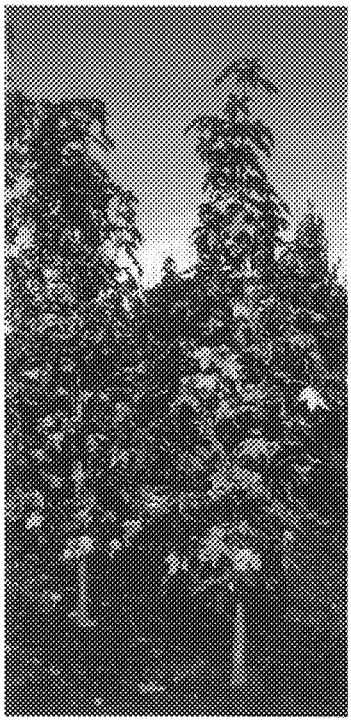
FIG. 1 is a close-up of two trees of my new variety with beginning fall colors and with some of the leaves showing the dark green summer color.
Figure 2:
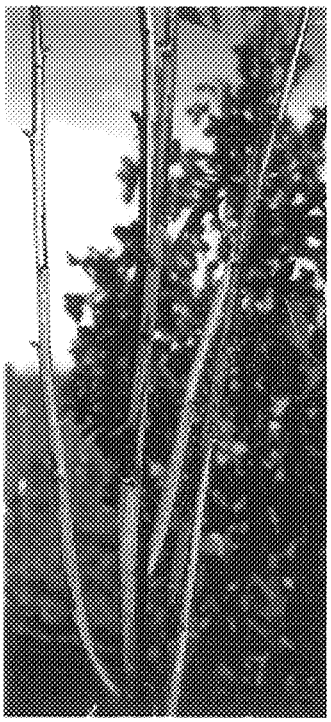
FIG. 2 is a close-up of branches of a tree of my new variety showing corky ridges on the branches and ascending branch orientation.
Figure 3:
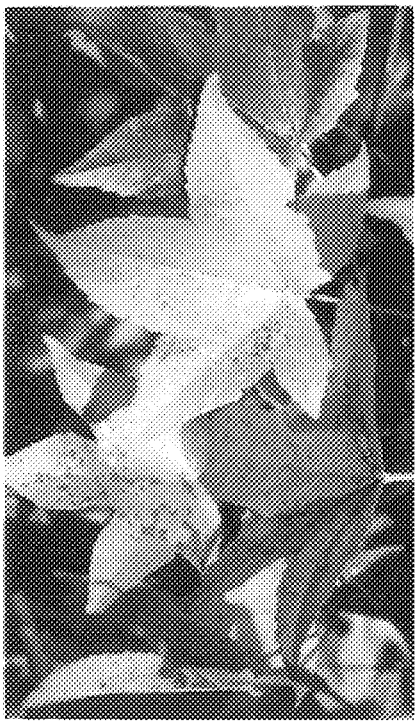
FIG. 3 is a close-up of leaves of the tree of my new variety showing the leaves as they change to their fall color.

My 'Clydesform' variety has not been observed under all growing conditions and thus variations may occur as a result of different growing conditions. The following is a detailed description of my new variety of sweet gum tree with color terminology in accordance with The Royal Horticultural Society Colour Chart (R.H.S.), published by The Royal Horticultural Society of London. The observations are of trees growing in Boring, Oreg.

The Plant

Parentage: Chance seedling of unknown origin found growing in a cultivated area of my nursery in Eugene, Lane County, Oreg.

Three shape: Columnar with stiffly ascending branches.

Trunk: Sturdy, straight.

Bark: Smooth on young stems with slight corky ridges vertically, becoming rough, furrowed and very corky by the fourth year. Corky ridges develop on vigorously growing branches during the first growing season.

*Immature bark color.*—Greyed-green R.H.S. 191B with greyed orange R.H.S. 165C corky ridges developing.

*Mature bark color.*—Grey-brown R.H.S. 199D.

Branches: Sturdy, very upright in orientation, round in cross section, developing rough, greyed-orange R.H.S. 165B ridges.

*Immature twig color.*—Yellow-green R.H.S. 146B with greyed-orange R.H.S. 165B corky ridges.

*Mature twig color.*—Yellow-green R.H.S. 148A with greyed-orange R.H.S. 165B corky ridges.

Leaves: Alternate, simple, palmately lobed with five triangular pointed lobes. Under vigorous growing conditions, one additional small lobe may occasionally form on the proximal lobes.

*Base.*—Leaf base cordate.

*Tips.*—Lobe tips acuminate.

*Serration.*—Finely serrate.

*Pubescence.*—Glabrous above. On the underside of the leaf, tufts of pubescence are found in the axils of the main and secondary veins, and veins are sparsely pubescent.

*Leaf surface.*—Smooth.

*Leaf color.*—Summer leaf color is unusually dark green with the upper leaf surface being green R.H.S. 139A and the lower (underside) leaf surface being yellow-green R.H.S. 146A. The fall color is yellow-orange R.H.S. 23B to greyed-orange R.H.S. 169B.

*Size.*—Variable, mature leaves typically 120 mm wide by 105 mm long (excluding the petioles).

*Stipules.*—Small papery stipules are attached to the petiole, originating 3 to 5 mm from the base of the petiole. They may dry up and not be visible by the end of the summer. Stipules lanceolate, 1 mm wide by 5 mm long.

*Petioles.*—Long, stout, In cross section, generally round except slightly flattened and grooved on top. Size: 5–9 cm. long by 2–4 mm thick. Color: Yellow green R.H.S. 144B.

Buds: Ovate, with 6–8 imbricate scales, 3–8 mm long by 1–4 mm wide, with the terminal and near the terminal buds being larger and the basal buds smaller. Yellow-green R.H.S. 144B.

Flowers: Perianth lacking, not showy. Female flowers in globose heads consisting of clusters of two beaked ovaries. Male flowers small, in terminal racemes.

Fruit: A spiny syncarp, 2 cm. Grey-orange R.H.S. 177A to Brown R.H.S. 200A in winter. Capsules dehiscent.

Growth rate: Relatively slow.

Distinguishing Characteristics

Columnar growth habit with a narrow overall shape and stiffly ascending branches. This shape, combined with its slow growth rate, makes it an ideal tree for resticted spaced.

Unusually dark summer leaf color, Green 139A. Seedling of *Liquidambar styraciflua* have leaves with a summer color which is closer to Green R.H.S. 137A in color.

Early development of corky ridges on bark. Corky ridges on my new cultivar develop on vigorous branches during the first growing season. On typical seedlings of the species, corky ridges are generally not seen until the second or third season.

Observations

Branch angle was measured at point of attachment as well as 75 cm along one year old branches on four year old 'Clydesform' variety and seedling sweet gum trees in the nursery. The branch angle (from vertical) of my new cultivar was virtually the same as that of these compared seedlings at the point of attachment to the trunk. However, unlike the compared seedings, the branches of trees of my new variety curve upwardly to become nearly parallel to the main trunk, giving my new cultivar a columnar habit. This is clearly demonstrated by the 10 degree measured branch angle (from vertical) found on branches 75 cm from their point of attachment. Measurements set forth in the table below are averages of measurements taken from twenty trees of my new vareity and twenty seedling trees growing side by side in a J. Frank Schmidt & So. Co. nursery in Boring, Oreg.

Tree height and tree width were measured for both four year old and eight year old specimens of my new cultivar as well as of the seedlings. The height to width ratio was calculated for each age, which shows the consistently narrow growth habit of my new cultivar. Measurements are averages of measurements of ten trees of each (of my new variety and of the compared seedlings) at age four, growing side by side, and of three trees of each at age eight, growing under similar nursery conditions.

| | New 'Clydesform' Cultivar | *Liquidambar styraciflua* Seedling |
|---|---|---|
| Branch Angle at point of attachment | 41 degrees | 44 degrees |
| Branch angle at 75 cm along limb: | 10 degrees | 42 degrees |
| 4 year old tree height | 1.7 meters | 2.5 meters |
| 4 year old tree width | 0.5 meter | 1.2 meters |
| 4 year old tree height to width ratio | 3.4:1 | 2.1:1 |
| 8 year old tree height | 4.7 meters | 5.7 meters |
| 8 year old tree width | 1.8 meters | 4.0 meters |
| 8 year old tree height to width ratio | 2.6:1 | 1.4:1 |

I claim:

1. A new and distinct variety of sweet gum tree substantially as herein shown and described, characterized particularly as to novelty by its columnar growth habit with a narrow overall shape and stiffly ascending branches, a relatively slow growth rate, unusually dark green summer leaf color and corky ridges which develop on vigorously growing branches during the first growing season.

* * * * *